(12) United States Patent
Muratsu (10) Patent No.: US 7,156,853 B2
(45) Date of Patent: Jan. 2, 2007

(54) MEASURING APPARATUS FOR TOTAL KNEE REPLACEMENT OPERATION

(75) Inventor: Hirotsugu Muratsu, Kakogawa (JP)

(73) Assignee: Zimmer Kabushiki Kaisha, Tokyo (JP)

( * ) Notice: Subject to any disclaimer, the term of this patent is extended or adjusted under 35 U.S.C. 154(b) by 315 days.

(21) Appl. No.: 10/669,419

(22) Filed: Sep. 25, 2003

(65) Prior Publication Data

US 2004/0122441 A1    Jun. 24, 2004

(51) Int. Cl.
*A61B 17/56* (2006.01)
(52) U.S. Cl. .................................................. 606/102
(58) Field of Classification Search .............. 606/86, 606/88, 89, 90, 99, 102, 104
See application file for complete search history.

(56) References Cited

U.S. PATENT DOCUMENTS 5,468,244 A * 11/1995 Attfield et al. ................ 606/90
5,514,143 A * 5/1996 Bonutti et al. ................ 606/86
5,540,696 A * 7/1996 Booth et al. .................. 606/88
5,911,723 A * 6/1999 Ashby et al. .................. 606/88
6,022,377 A * 2/2000 Nuelle et al. .................. 606/90
6,478,799 B1 * 11/2002 Williamson .................. 606/90

* cited by examiner

*Primary Examiner*—Eduardo C. Robert
*Assistant Examiner*—David Comstock
(74) *Attorney, Agent, or Firm*—Ditthavong & Mori, P.C.

(57) ABSTRACT

An apparatus in a total knee replacement and arthroplasty operation for measuring a joint gap and ligament balance between a osteotomized surface at a femoral distal end and a osteotomized surface at a tibial proximal end. The apparatus is provided with a base 10, from which an engaging plate 14 extends by way of an arm, so that the engaging plate 14 contacts with the osteotomized surface at the tibial proximal end. A moving body 18 is vertically movably connected to the base 10, from which moving body 18 an arm 20 extends, to which arm a supporting plate 22 is rotatably mounted about a central axis. The supporting plate 22 has, at its top surface, a projected portion 48. to which an auxiliary guiding piece 50 is connected under a snap like fitted manner. A femoral component 52 is mounted, at its groove portion 54, to the osteotomized surface at the femoral distal end. The engaging plate 14 as well as the supporting plate 22 are under an offset arrangement with respect to the base and moving body, respectively.

11 Claims, 8 Drawing Sheets

MEASURING APPARATUS FOR TOTAL KNEE REPLACEMENT OPERATION

BACKGROUND OF THE FIELD OF THE INVENTION

1. Field of the Invention

The present invention relates to an apparatus used for a surgical operation, in particular, to an apparatus used in a total knee replacement (TKR) operation and a total knee arthroplasty (TKA) operation for measuring a gap (joint gap) between osteotomized surfaces at a femoral distal end and a tibial proximal end as well as an inclination between the osteotomized surfaces (ligament balance).

2. Description of Related Art

In the knee replacement and arthroplasty operation, a replacement to knee prosthesis (tibiofemoral (T-F) joint) is done. Known in a prior art is a knee prosthesis, which includes a femoral component made of a metal material and fixed to an osteotomized surface at a femoral distal end, a tibial plate made of a metal material and fixed to an osteotomized surface at a tibial proximal end, and a surface component made of a plastic material such as a polyethylene and arranged between the femoral component and the tibial plate. In such a type of knee prosthesis, it is desired that a flexion and extension of tibiofemoral joint along a wide range of knee flex angle such as 150 degree must be possible. In view of this, the femoral component is smoothly curved such that the femoral component covers the entire osteotomized surface, which extends from an anterior part and a posterior part, of the femoral bone. In addition, the surface component made of the polyethylene material on the osteotomized surface at a tibial proximal end is formed such that the surface component has a shape, which is matched to the outer shape of the femoral component along the entire range of the knee motion.

During the execution of the total knee replacement operation, a precisely mounted condition of all of the components constructing knee joint is essential. In order to obtain such a condition, a possibility of a desired adjustment is essential as to a gap between osteotomized surfaces at a femoral distal end and a tibial proximal end as well as an inclination between these osteotomized surfaces. In view of this, during the execution of the surgical operation, a measurement of the gap as well as the inclination is done, while applying a tension of a predetermined value in a media and lateral collateral ligaments and in a patellar tendon, and, then, if a desired value of the gap or a desired value of the inclination is not obtained, a suitable relaxation or detachment of the media or lateral collateral ligament (soft tissues) attached to the femoral and tibial bones is done, thereby adjusting the gap or inclination or the both. Such a gap and inclination measurement as well as an adjustment of the same are, conventionally, done at both of extended and flexed conditions of the knee.

U.S. Pat. No. 5,911,723 of Ashby et al. proposes a measuring apparatus (so-called tensor) for measuring a gap between femoral and tibial osteotomized surfaces and a ligament balance, which apparatus includes a base having an engaging surface contacting with an osteotomized surface at a tibial bone and a moving head vertically movable with respect to the base and having an engaging surface contacting with an osteotomized surface at a femoral bone. The base and the moving head are connected with each other by means of a latchet mechanism. A measurement of the gap is done, while applying a predetermined value of load between the tibial and femoral bones, so that a measured value of the gap is displayed. In Ashby et al., the engaging surface of the moving head for a contact with the osteotomized surface at a femoral bone is rotatable about an axis, which is parallel with respect to the osteotomized surface. As a result, a ligament imbalance causes the engaging surface of the moving head to be inclined and the corresponding value of inclination (ligament balance) is able to be directly read out from a scale.

In Ashby et al., both of the tibial and femoral engaging surfaces extend, in a straight manner, anteriorly from the base and the moving head, respectively. Such a straight arrangement prevents the apparatus from being inserted between the femoral and tibial osteotomized surfaces without patellar eversion. Namely, in order to allow the apparatus to be installed, a patella eversion is done laterally from a medial skin incision line, thereby generating a space for an installation of the device. Furthermore, the patella eversion is maintained during the entire period for the measurement of the gap as well as the ligament balance.

As fully described above, in Ashby et al., it is essential that the gap and the ligament balance are measured while the patella eversion is maintained. Namely, with such a patella eversion, the patella is displaced or retracted laterally of the knee, thereby generating a space at the anterior side of the knee for the movable head and the base, which extend anteriorly from the upper and the lower engaging surfaces, which are engaged the femoral and tibial osteotomized surfaces, respectively. Such a measurement of the gap and ligament balance with the patella eversion is not desirable from the view point that a measurement during operation is done under a condition of the knee, which is quite different from a physiological condition of the knee after the completion of the operation.

Furthermore, in Ashby et al., the upper and the lower engaging surfaces are directly connected to the femoral and tibial osteotomized surfaces, respectively. A knee extension gap is measured as a gap between the osteotomized surfaces when a parallel relationship in anteroposterior direction is obtained between the upper and the lower engaging surfaces of the measuring apparatus. As far as the femoral distal end is concerned, the osteotomized surface is orthogonal (90° cut) to the longitudinal axis of the bone. The osteotomized surface at the tibial proximal end is, however, inclined (less that 10°) with respect to the axis of the bone in accordance with the shape of the tibial component. This means that the measurement in the Ashby et al. is influenced by the condition of the opposed osteotomized surfaces between the femoral bone and the tibial bone. Furthermore, the measurements at the extended condition (less than 180°) and the flexed condition (90°) are only possible, i.e., Ashby et al. does not make it possible to measure at any desired knee flexion angle.

SUMMARY OF THE INVENTION

An object of the present invention is to provide a measuring device capable of overcoming the above-mentioned difficulties in the prior art.

Another object of the present invention is to provide a measuring apparatus capable of effecting the measurement of the gap as well as ligament balance without patellar eversion.

Still another object of the present invention is to provide a measuring apparatus capable of effecting the measurement of the gap as well as ligament balance at any desired knee angle.

According to the first aspect of the present invention, an apparatus in a total knee replacement operation is provided for measuring a joint gap and ligament balance between an osteotomized surface at a femoral distal end and a osteotomized surface at a tibial proximal end, said apparatus comprising:

a base;

a first engaging member on said base for an engagement with said osteotomized surface at the tibial proximal end;

a moving body;

a second engaging member on said moving body for an engagement with said osteotomized surface at said femoral distal end, said second engaging member being rotatable on the moving body about an axis substantially parallel with respect to said osteotomized surface at the femoral distal end;

said base and moving member being connected with each other so that the first and second engaging members are selectively moved between a direction where the first and second engaging members are moved toward each other and a direction where the first and second engaging members are moved away from each other;

a driving member, by which said moving member is moved with respect to the base so that the first and second engaging members are moved in the direction away from each other motor;

an locking member on the moving body, said stopper member engaging with the driving member for locking the movement of the driving member in the direction where the first and second engaging members are moved toward each other;

a first indicator indicating the value corresponding the spacing between the first and second engaging members, and:

a second indicator indicating the value corresponding the angle between the first and second engaging members, said first and second engaging members being under an offset arrangement with respect to said base and moving body, respectively.

In the operation of this aspect of the invention, prior to the installation of the apparatus according to the present invention, a patellar eversion is done in a lateral direction from a skin incision location. Then, the first and second engaging members are inserted to a space between osteotomized surfaces at a femoral distal end and a tibial proximal end, in such a manner that the first engaging member is engaged with the osteotomized surface at the tibial proximal end and the second engaging member is engaged with the osteotomized surface at the femoral distal end. Under the condition that the first and the second engaging members are engaged respectively with the osteotomized surfaces at the femoral distal end and the tibial proximal end is obtained, the patellar eversion is cancelled, so that the patellar is returned to a non-everted physiological position. In other words, the offset arrangement of the fist and second engaging members with respect, respectively, to the base and the moving body makes it possible to obtain a condition that the base and the main body are located at positions not intervened with the patella. In this condition, the driving member is operated by a tool such as a torque wrench, in such a manner that the spacing between the first and second engaging members is increased against the tension generating in the soft tissues stabilizing the knee tissues. The driving member is locked by a suitable means such as a latchet mechanism when a predetermined force is generated in the driving member. On this locked condition, a reading of the first scale is obtained, which corresponds to the value of the gap between the tibial osteotomized surface and the femoral osteotomized surface. Furthermore, a reading of the second scale is obtained, which corresponds to an inclination between the tibial osteotomized surface and the femoral osteotomized surface, i.e., degree of imbalance in ligament. A very important advantage of the offset arrangement of the first and second engaging members with respect to the base and the moving body, respectively, according to the present invention is that the gap as well as the imbalance are measured without any substantial patella eversion, i.e., under a intrinsic position of the patella which is directed anteriorly. As a result, a measurement of the gap as well as imbalance becomes possible without any adverse effect, which otherwise would occur when a measurement is done with patella eversion. In other words, according to the present invention, a measurement can be done under an intrinsic condition of the knee from the view point of physiology.

According to the second aspect of the present invention, an apparatus is provided for use in a total knee replacement operation for measuring a joint gap and ligament balance between an osteotomized surface at a femoral distal end and an osteotomized surface at a tibial proximal end, said apparatus comprising:

a femoral component for an insertion to the osteotomized surface at a femoral distal end;

a base;

a first engaging member on said base for an engagement with said osteotomized surface at the tibial proximal end;

a moving body;

a second engaging member on said moving body for an engagement with said osteotomized surface at said femoral distal end, said second engaging member being for mounting thereon said femoral component, said second engaging member being rotatable on the moving body about an axis substantially parallel with respect to said osteotomized surface at the femoral distal end;

said base and moving member being connected with each other so that the first and second engaging members are selectively moved between a direction where the first and second engaging members are moved toward each other and a direction where the first and second engaging members are moved away from each other;

a driving member, by which said moving member is moved with respect to the base so that the first and second engaging members are moved in the direction away from each other motor;

an locking member on the moving body, said stopper member engaging with the driving member for locking the movement of the driving member in the direction where the first and second engaging members are moved toward each other;

a first indicator indicating the value corresponding the spacing between the first and second engaging members, and:

a second indicator indicating the value corresponding the inclination between the first and second engaging members.

In this aspect of the invention, the first and second engaging members are inserted to a space between osteotomized surfaces at a femoral distal end and a tibial proximal end, in such a manner that the first engaging member is engaged with the osteotomized surface at the femoral distal end and the second engaging member is engaged with the osteotomized surface at the tibial proximal end. The femoral component for a patient, which is inserted to the osteotomized surface at the femoral distal end, is engaged on the second engaging member. In other words, a condition is obtained, where the first engaging member is engaged with the osteotomized surfaces at the femoral distal end and the second engaging members is engaged with the osteotomized surfaces at the tibial proximal end, on which the femoral component is inserted. In this condition, the driving member is operated by a tool such as a torque wrench, in such a manner that the spacing between the first and second engaging members is increased against the tension generating in the soft tissues around the knee. The driving member is locked by a suitable means such as a latchet mechanism when a predetermined force is generated in the driving member. On this locked condition, a reading the first scale is obtained, which corresponds to the value of the gap between the tibial osteotomized surface and the femoral component. Furthermore, a reading of the second scale is obtained, which corresponds to an inclination between the tibial osteotomized surface and the femoral component, i.e., degree of imbalance in ligament. A very important advantage of this aspect of the present invention is that the femoral component is inserted to the femoral distal end and that the measurement of the gap as well as the ligament balance is done under the condition that the femoral component is rested on the second engaging member. By the insertion of the femoral component onto the second engaging member, the femoral bone is able to flex with respect to the tibial bone at a desired inclination during the measurement. In other words, the measurement of the gap as well as the ligament balance can be done under a desired knee flexion angle regardless with the cut angle of osteotomized surfaces.

Preferably, said second engaging member may have, at its surface remote from the first engaging member, a fitting part, and wherein the device further comprises an auxiliary guiding member for a fitted engagement with said fitting part on the second engaging member and engaged with the femoral component. In this preferred construction, the auxiliary guiding member guides the femoral component in such a manner that a smooth movement of the femoral component with respect to the second engaging member is obtained along a desired range of angle of the femoral bone with respect to the tibial bone. Furthermore, a plurality of the guiding member of different sizes can be prepared respectively for the different sizes of the existing different sizes of femoral components, while the guiding member of different sizes can be inserted to the second engaging member. As a result, a selection of a desired size of a guiding member matched to a particular size of a femoral component matched to the particular patient allows the femoral component to be fitted to the fitting part on the second engaging member. In other words, with respect to the various sizes of the femoral components, the measurement of the gap as well as the ligament balance is realized by one and same measuring apparatus (tensor) so long as a suitable size of the guiding member matched to the femoral component inserted to the patient is selected.

Preferably, said fitting engagement between the fitting part of the second engaging member and the auxiliary guiding member is done under a snap engaging fashion. The snap engagement allows, on one hand, the auxiliary guiding member to be firmly held on the second engaging member during the measurement and, on the other hand, the auxiliary guiding member to be easily removed after the completion of the measurement.

DESCRIPTION OF PREFERRED EMBODIMENT

Figure 1:
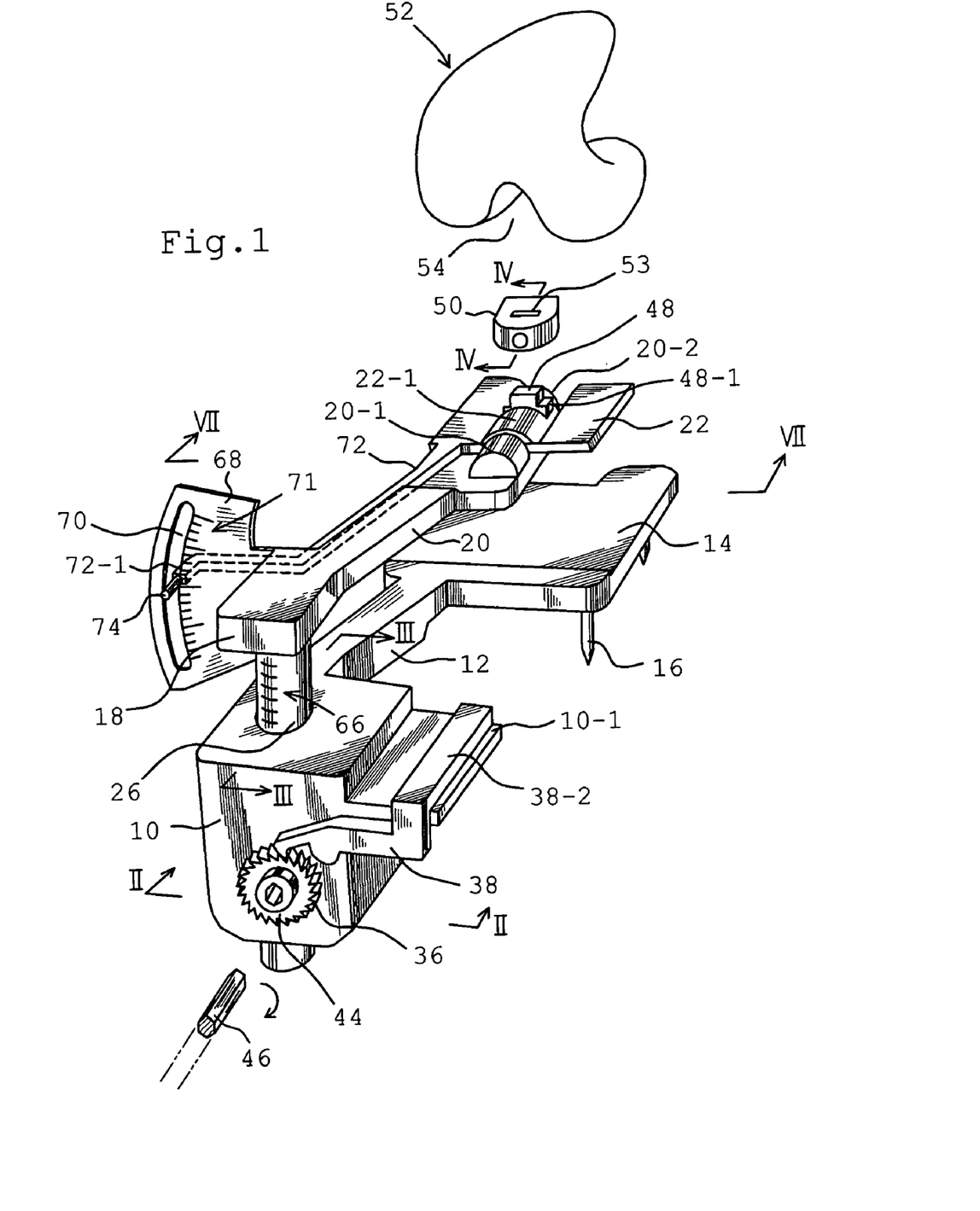
FIG. 1 is an entire perspective view of a measuring apparatus according to the present invention.
Figure 6:
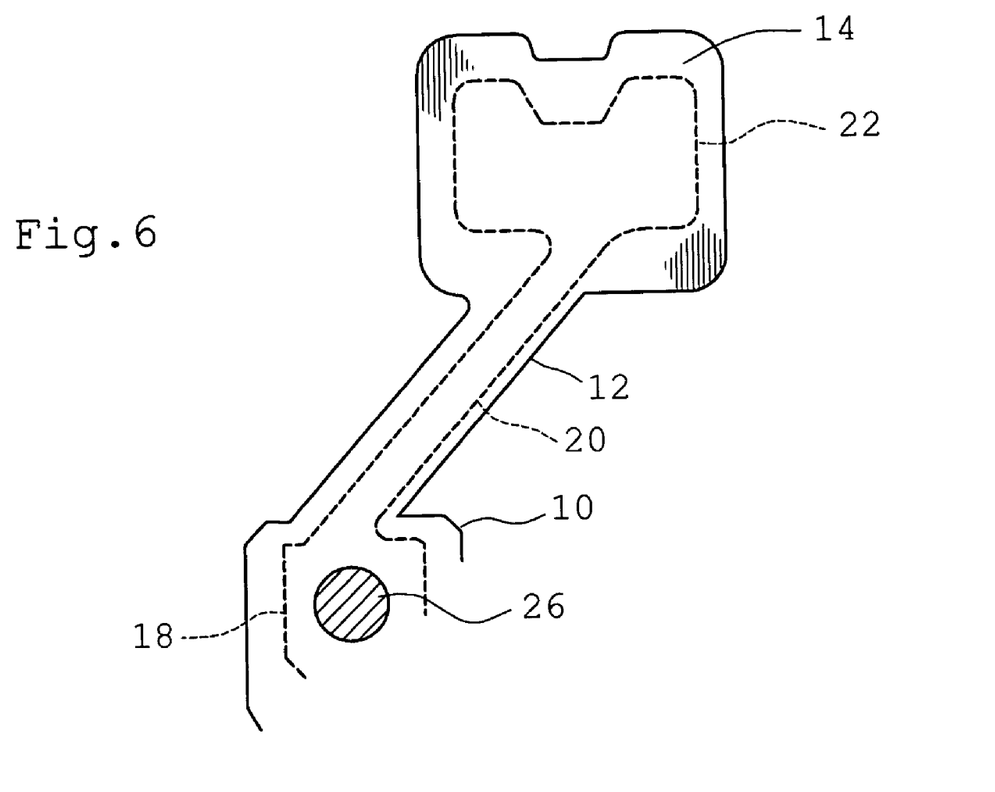
FIG. 6 is a schematic plan view of the apparatus and illustrating an offset arrangement of an engaging plate and a supporting plate with respect to a base and moving member, respectively.

Now, an embodiment of a measuring apparatus for according to the present invention for an apparatus for measuring a joint gap and a ligament balance during the execution of a total knee replacement and arthroplasty operation will be explained with reference to attached drawings. In FIG. 1, a reference numeral 10 denotes a base having an upper part, from which an arm 12 is extended in a cantilever fashion. The arm 12 is, at its free end, integrally formed with an engaging plate 14. The engaging plate 14 is, at its lower surface, formed with fixing nails 16 of a desired number and extending downwardly. The nails 16 are for a fixation of the engaging plate 14 to an osteotomized surface at a tibial proximal end, as will be explained later in more detail with reference to FIGS. 7 and 8. In FIG. 1, the shown measuring apparatus is for an installation to a left-handed knee joint. The important feature of the present invention is that the engaging plate 14 on the tibial osteotomized surface is under an offset relationship with respect to the base 10 such that, with respect to the patella, the base 10 is displaced inwardly to the side, from which a skin expansion is made. Such an offset arrangement between the engaging plate 14 and the base 10 is the most clearly illustrated in FIG. 6.

Figure 7:
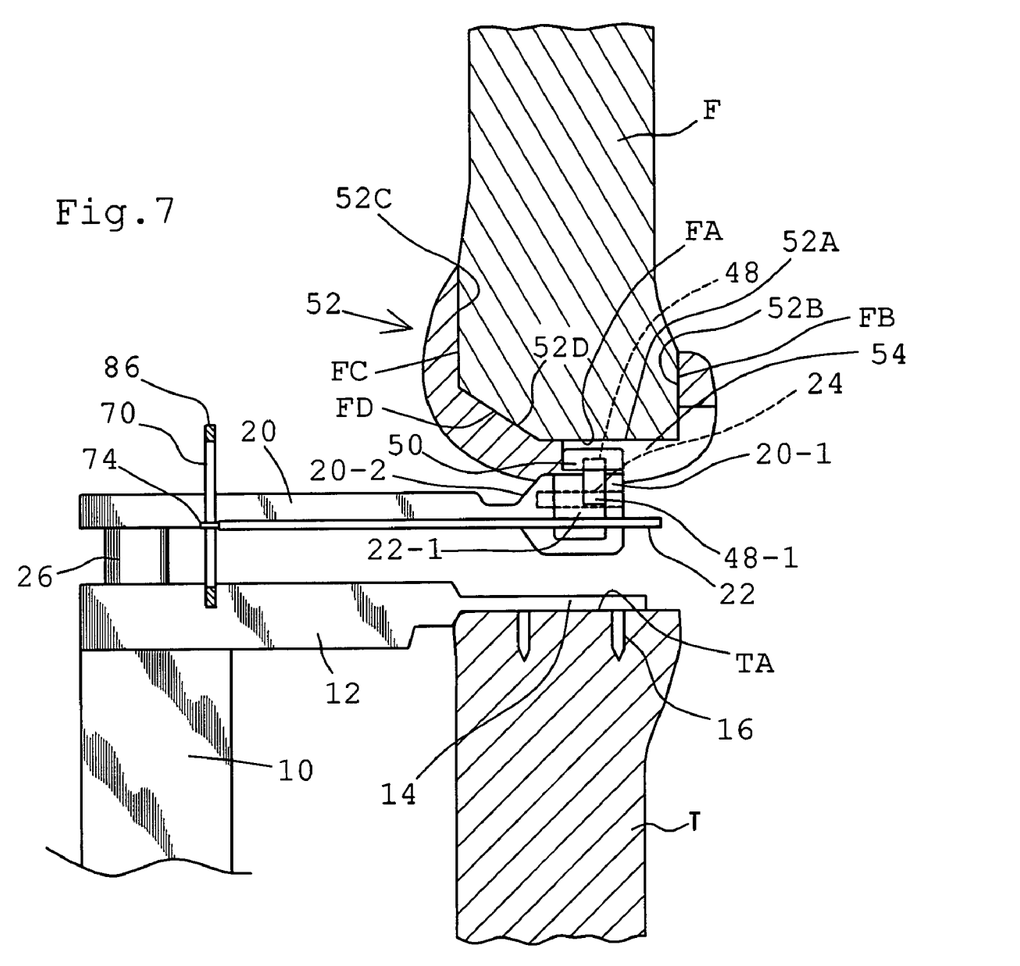
FIG. 7 is a side view of a measuring apparatus taken along a line VII—VII in FIG. 1 when an extended gap is measured.

In FIG. 1, a reference numeral 18 denotes a moving body, from which an arm 20 extends in a cantilever fashion. At a free end of the arm 20, a supporting plate 22 is provided in such a manner that the supporting plate 22 is rotatable about an axis parallel to the osteotomized surface at a femoral distal end. The arm 20 is, at its free end, integrally formed with a pair of spaced tubular supporting portions 20-1 and 20-2, to which a pin 24 (FIG. 7) is inserted. As shown in FIGS. 1 and 7, the supporting plate 22 is, at it middle portion, provided with a boss portion 22-1, which is located between the paired tubular supporting portions 20-1 and 20-2. Furthermore, the pin 24 mounted between the supporting portions 20-1 and 20-2 is freely passed through a central bore of the boss portion 22-1. As a result, the supporting plate 22 is made rotatable about an axis of the pin 24, which axis is orthogonal to the plane of the paper of FIG. 9. A relationship between the supporting plate 22 and moving body 18 is also an offset one, as similar to that between the engaging plate 14 and the base 10. Namely, the moving body 18 is displaced inwardly from the patellar to the side where the skin incision is made.

Figure 2:
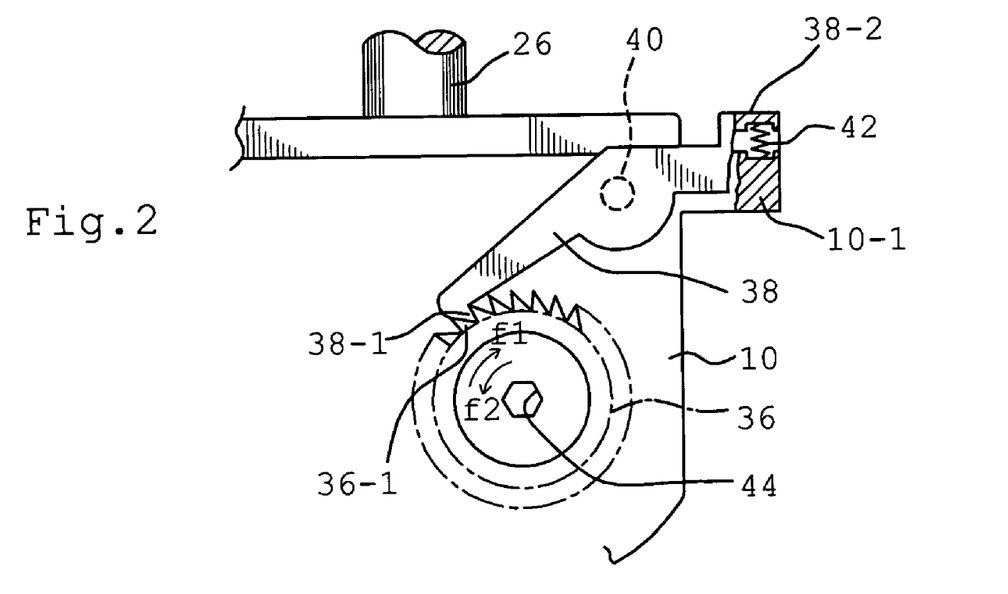
FIG. 2 is a view taken along a line II—II in FIG. 1 and illustrating a construction of a ratchet mechanism.
Figure 3:
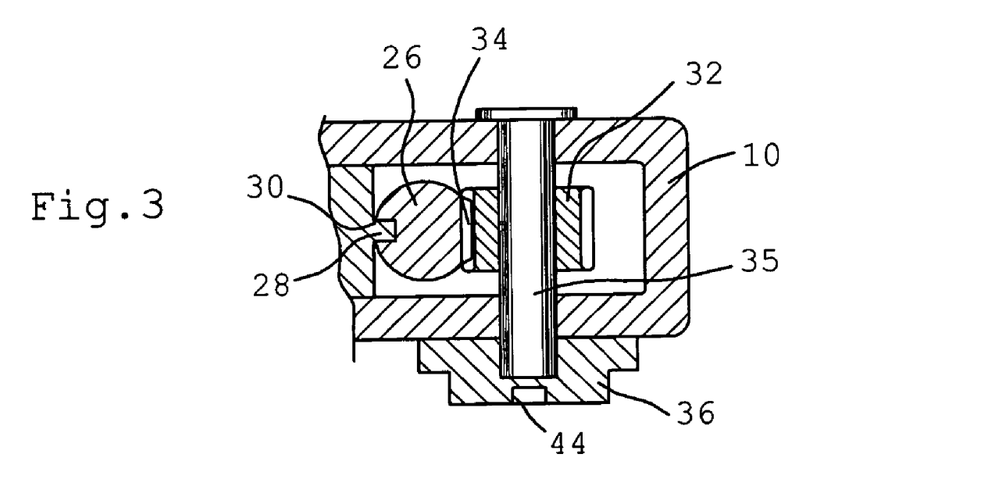
FIG. 3 is a view taken along a line III—III in FIG. 1 and illustrating a construction of a rack-gear mechanism.

In FIG. 1, a guiding means is provided, which allows the moving body 18 to be vertically movable with respect to the base 10. The guiding means includes a supporting shaft 26 which is integral to the moving body 18 and which is located in a hollow space extending vertically in the moving base 10. Furthermore, the base 10 is, at its inner wall, formed with a guide key 28 extending in a vertical direction, which corresponds to the direction, orthogonal to the surface of the paper of FIG. 3. The guide key 28 is engaged with a guide slot 30, which is formed in the supporting shaft 26 along a longitudinal direction. The longitudinal direction is orthogonal to the surface of the paper of FIG. 3. That is, the supporting shaft 26 integral with the moving body 18 is vertically slidably guided with respect to the base 10. And then, a driving means is provided for driving the engaging plate 14 of the base 10 and the supporting plate 22 of the moving body 18, so that the engaging plate 14 and the supporting plate 22 can move in directions toward each other or in directions away from each other. As shown in FIG. 3, the driving means is comprised of a pinion 32, a rack 34 formed on a part of the surface of the supporting shaft 26 so as to intermesh with the pinion 32, and a rotating shaft 35 for supporting the pinion 32 on the opposite wall of the base 10. As stated above, the guide slot 30 of the supporting shaft 26 is engaged with the guide key 28 of the base 10 for a vertically movement along the axis while preventing any rotating movement about the axis. As a result, when the pinion 32 is subjected to a rotating movement, the supporting shaft 26, which is made integral with the rack 34 intermeshing the pinion 32, is vertically elevated in the direction orthogonal to the paper of FIG. 3. According to the present invention, the driving means is provided with a means for locking or locking a downward movement of the moving body 18 toward the base 10, which the binding means is formed as a ratchet mechanism. This ratchet mechanism includes a ratchet wheel 36 and a ratchet lever 38 as shown in FIG. 2. The ratchet wheel 36 is fixed at one end of the rotating shaft 35 outside of the base 10 and the ratchet lever 38 is rotationally mounted on the sidewall of the base 10 by using a pin 40 as shown in FIG. 2. The ratchet lever 38 has, at its one end, a pawl portion 38-1, which is selectively capable of engaging with the tooth portion of the ratchet wheel 36. The other end portion 38-2 of the ratchet lever 38 is arranged so as to oppose to a shelf portion 10-1 in a small distance, which the shelf portion is an extended portion of the sidewall of the base 10. A spring 42 is arranged between the opposing surfaces of 38-2 and 10-1 of the ratchet lever 38 and base 10. The spring 42 biases the ratchet lever 38 to rotate in a counterclockwise direction in FIG. 2 about the axis of the pin 40, so that the pawl portion 38-1 at the end of the ratchet lever 38 engages with one of teeth 36-1 of the ratchet wheel 36, thereby preventing the ratchet wheel 36 from its rotation in a usual state of the apparatus. Accordingly, a rotational motion of the pinion 32 meshing with the rack 34 on the supporting shaft 26, i.e., a vertical movement of the supporting shaft 26 as well as the moving body 18 does not occur.

As shown in FIG. 2, the tooth 36-1 of the ratchet wheel 36 has the front portion gently sloped in a clockwise direction (arrow f1) and the rear portion steeply sloped (perpendicular direction) in a counterclockwise direction (arrow f2). Therefore, in the rotational motion in the counterclockwise direction f2, the teeth of the ratchet wheel 36 cannot climb over the pawl portion 38-1 at the end of the ratchet lever 38 due to its steeply sloped surface. Contrary to this, in the rotational motion in the clockwise direction (arrow f1), the teeth of the ratchet wheel 36 can climb over the pawl portion 38-1 at the end of the ratchet lever 38 due to the gently sloped surface, so that the toothed wheel 32 can drive the rack 34 in an upward direction (perpendicular to the paper of FIG. 3) by the rotational motion of the ratchet wheel 36 in the arrow f1 direction. And as shown in FIG. 1, the ratchet wheel 36 is provided with a tool engaging cutout 44 of a hexagonal cross-sectional shape on its sidewall, so that it is possible to generate the f1 directional rotation of the ratchet wheel 36, which is the clockwise directional rotation in FIG. 2, by fitting a tip of a torque wrench 46 of a hexagonal cross-sectional shape into the tool engaging cutout 44 in order to upwardly move the supporting shaft 26, i.e., the moving body 18. The torque wrench 46 has a known limiting mechanism of a rotational torque, which allows the upward movement of the moving body 18 (increase of the gap between the engaging plate 14 on the tibial side and the supporting plate 22 on the femur side) by the clockwise directional (f1) rotation of the ratchet wheel 36, which is to be carried out until a predetermined value of the rotational torque is obtained. Also, the other end portion 38-2 of the ratchet lever 38 is pushed down against the spring 42 to rotate the ratchet lever 38 somewhat around the pin 40 in the clockwise direction, which allows the pawl portion 38-1 at the end of the ratchet lever 38 to be disengaged from the tooth 36-1 of the ratchet wheel 36, which leads the toothed wheel 32 to freely rotate, thus the supporting shaft 26, i.e., the moving body 18 can be freely vertically moved.

As shown in FIG. 1, the boss portion 22-1 of the supporting plate 22 is, at its upper surface, formed with a projected portion 48, to which a femoral component 52 is fitted by way of an auxiliary guiding piece 50, which functions as a guiding member for causing the femoral component 52 to turn around within the range of the flexion and extension of the knee. Note that, the femoral component fitted for a gap measurement, which will be stated later, is not one for the patient but a femoral component of all the same in size for testing (trial) in order to prevent the femoral component for the patient from being damaged during measuring period. The femoral component 52 has, as shown by a schematic sectional view in FIG. 7, a vertical cross-sectional shape surrounding the femur distal end. In other words, the femoral component 52 has a shape, which covers a femoral distal end at a region between the anterior portion and the posterior portion. As a result, the femoral component 52 allows the knee to be moved in a desired range between an extended condition and a flexed condition. In addition, the outer surface of the femoral component has a curved surface, which contacts with a surface component (not shown) made of polyethylene inserted on a tibial plate (not shown). As is clear in FIG. 7, the femoral component 52 has an inner surface contacting with the femoral bone F, which inner surface is constructed by a first part 52A opposing to a tip osteotomized surface FA, a second part 52B opposing to a posterior osteotomized surface FB, a third part 52C opposing to a anterior osteotomized surface FC, and a fourth part 52D opposing to a anterior beveled surface FD. An elongated and narrow guiding channel 54 is formed on the bottom surface of the femoral component 52, which extends from a bottom surface to a posterior surface of the femoral bone. The guide channel 54 functions to receive a stabilizer of the polyethylene surface component on the tibial plate on the tibial bone after the insertion of the knee prosthesis is completed. That is, in the present invention, since the auxiliary guiding piece 50 on the supporting plate 22 engages with the guiding channel 54 of the femoral component 52, the auxiliary guiding piece 50 performs a guiding function as if it were the stabilizer on the tibial plate in the fully completed state of the total knee replacement operation, so that a smooth movement of the femoral component 52 is obtained between an extended state (FIG. 7) and a flexed state (FIG. 8) of the knee during an execution of a measurement of the joint gap and a ligament balance.

Figure 4:
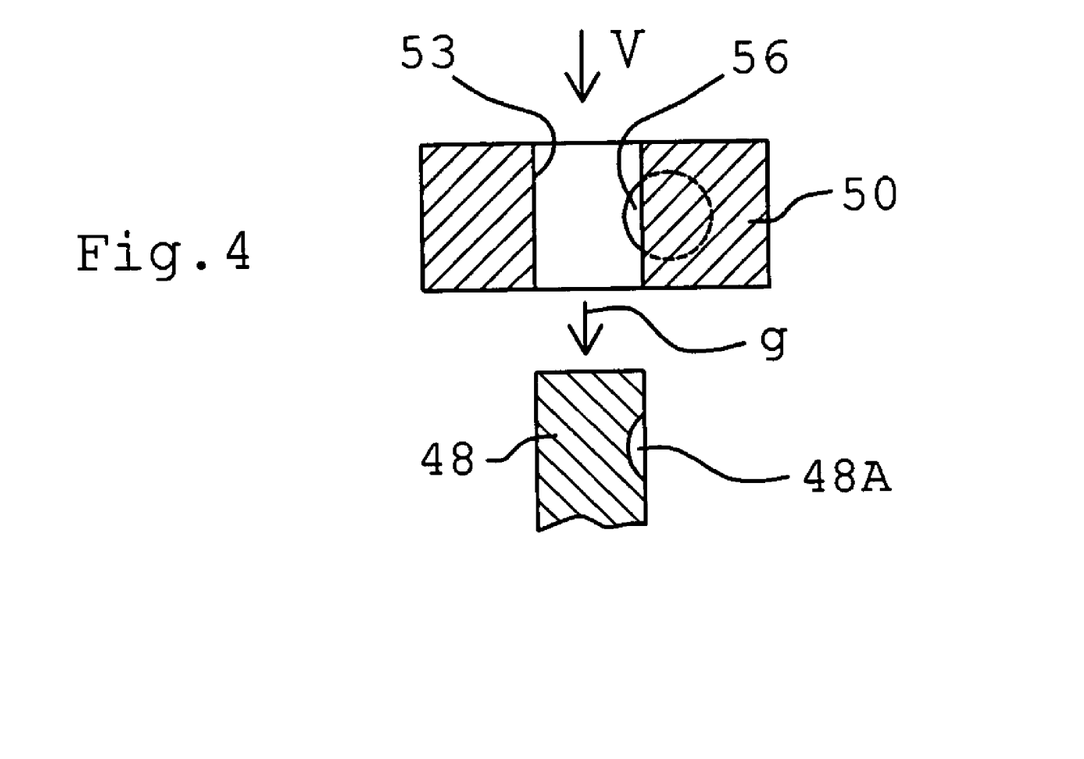
FIG. 4 is a cross-sectional view taken along a line IV—IV in FIG. 1 and illustrating a construction of an auxiliary guiding member.
Figure 5:
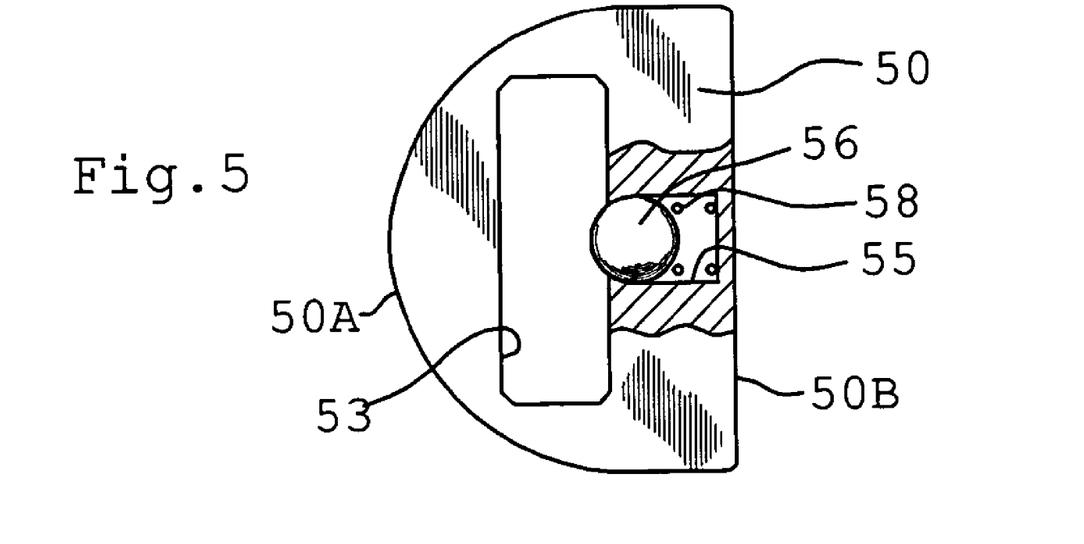
FIG. 5 is a view taken along a line V in FIG. 4.
Figure 8:
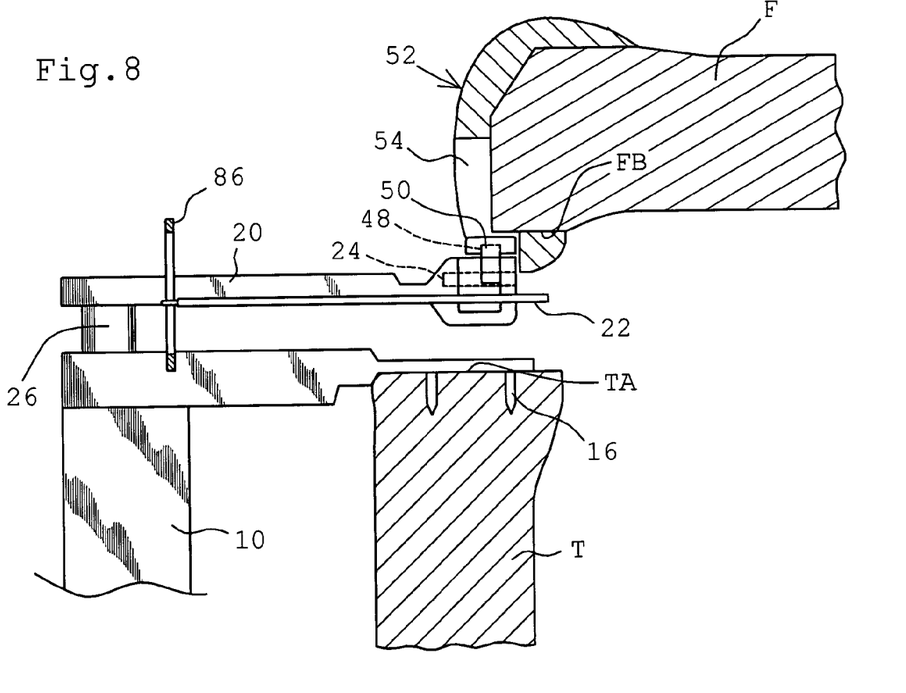
FIG. 8 is the same as FIG. 7 but illustrates a measurement of flexion gap, when a flexion gap is measured.

As shown in FIG. 5, the auxiliary guiding piece 50 is adapted to be mounted to the raised portion or projection 48 on the supporting plate 22. Namely, the auxiliary guiding piece 50 has a rounded front surface 50A, a rear flat end surface 50B, and a slot 53 of an elongated rectangular cross-sectional shape, which extends completely through the auxiliary guiding piece 50. This slot 53 has a dimension, which allows the raised portion 48 to be smoothly inserted and to be neatly fitted, resulting in a stable mounted condition of the auxiliary guiding piece 50 on the supporting plate 22. In addition, the auxiliary guiding piece 50 is provided with a closed-end cavity 55 opening laterally to the inner wall of the slot 53. A spherical member 56 is stored in the closed-end cavity 55 and a spring 58 is provided for urging the spherical member in such a manner that the spherical member 56 is partly protruded to the slot 53. However, an opening portion of the closed-end cavity 55 is somewhat narrowed to prevent the spherical member 56 from being dropped out of the slot 53. During the mounting of the auxiliary guiding piece 50 to the raised portion 48 on the supporting plate 22 along an arrow g in FIG. 4, the spherical member 56 is, first, contacted with the raised portion 48, which causes the spherical member 56 to be pushed inwardly and moved toward the bottom of the closed-end cavity 55 against the force of the spring 58. The raised portion (projection) 48 is one piece member of the boss portion 22-1 of the supporting plate 22 and extends upwardly from the foundation portion 48-1 as shown in FIG. 8. Furthermore, the raised portion 48 has a slightly narrowed width over that of the foundation portion 48-1, as shown in FIG. 1. The insertion of the auxiliary guiding piece 50 to the projected portion 48 via the slot 53 causes, finally, the piece 50 to be engaged with the foundation portion 48-1 under a face-to-face contact relationship, thereby obtaining a stabled fixed condition of the auxiliary guiding piece 50 on the supporting plate 22. Further, as shown in FIG. 4, formed on the rear surface of the raised portion 48 is a recess 48A, with which the spherical member 56 is engaged under a spring force by the spring 58. In other words, a snap engagement of the auxiliary guiding piece 50 with respect to the projected portion 48 is obtained, resulting in a firmly fixed condition of the auxiliary guiding piece 50 on the projected portion 48. This does not cause the piece 50 to be difficult in its removal. Namely, upon an upward movement of the piece 50 in the direction opposite to the arrow g in FIG. 4, the spherical member 56 is moved inwardly against the force of the spring 58 in the slot 55 under the cam like action of the recess 48A with respect to the spherical member 56, thereby allowing the auxiliary guiding piece 50 to be easily detached from the projected portion 48, i.e., the supporting plate 22.

With respect to the outer shape or dimension, the auxiliary guiding piece 50 is shaped in accordance with the guiding channel 54 of the femoral component 52 to be fixed to the supporting plate 22. Namely, as far as the femoral components are concerned, there are patient-to-patient changes in their dimensions or sizes. For example, there are changes in the width and/or depth of the guiding channel 54 between femoral components 52. Therefore, so long as a variety of auxiliary guiding pieces 50 are provided in accordance with the varied sized of the guiding channels 54 in a variety of femoral components 52, while keeping the same the dimensions (length, width and depth) of the slot 53 between the varieties of auxiliary guiding pieces 50, gap measurement for various patients, i.e., a variety of femoral components can be carried out by using the common or the single measuring apparatus for.

Next, a measuring operation of a gap and a ligament balance of the measuring apparatus according to the present invention will be explained. With reference to FIG. 1, a scale or graduation 66 for a gap indication is formed on the shaft at a location below the connecting portion of the supporting shaft 26 to the moving body 18, so that it is possible to directly read the gap between the osteotomized surfaces of the femoral bone and the tibial bone by reading a value of the graduation 66 on the same plane as that of the base 10. In place of the graduation, a scale plate may be fixed to the moving body 18 and cooperates with an edge of the base 10, which allows a gap to be read out from the scale plate.

Figure 9:
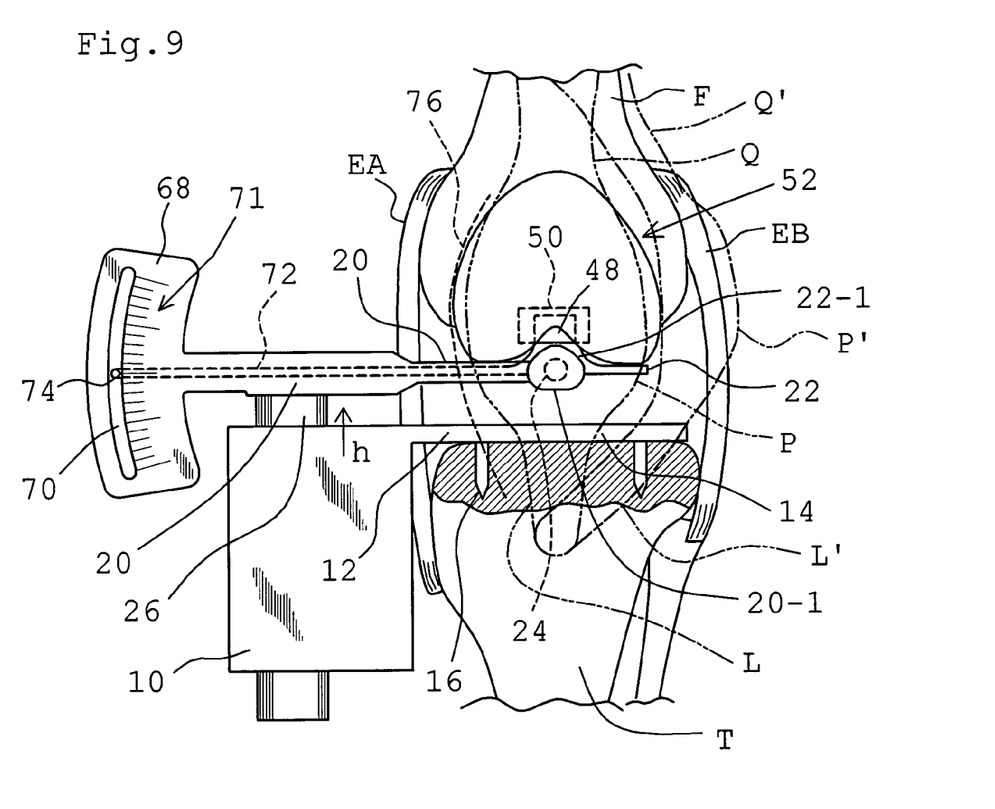
FIG. 9 is a front view of the measuring apparatus and illustrates a measurement of a ligament balance.
Figure 10:
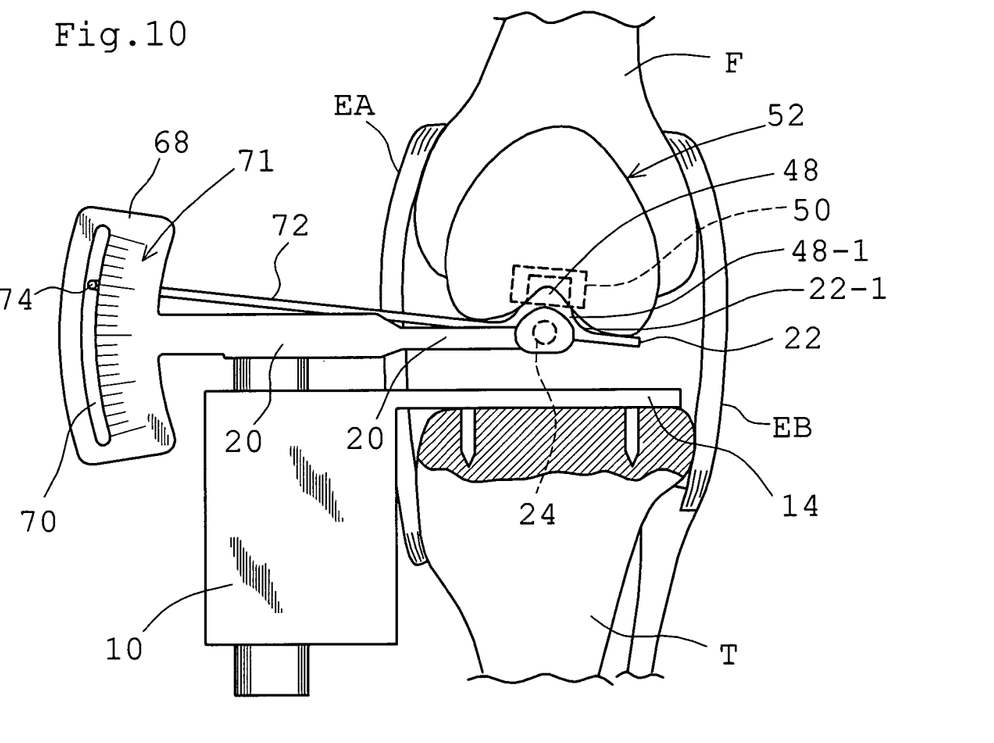
FIG. 10 is the same as FIG. 9 but illustrates the apparatus when a degree of imbalance exists.

A scale plate 68 extending vertically outside of the moving body 18 is provided in one piece with the moving body 18, a bow shaped slot 70 (refer to FIG. 9 for the shape of the slot 70) is formed on the scale plate 68, and a scale or graduation 71 is formed on the exterior of the scale plate 68 along the slot 70. On the other hand, as shown in FIG. 1, an arm 72 is extended from the supporting plate 22 approximately parallel to the arm 20. The arm 72 has a tip portion 72-1, which is bent forward by 90 degree. Furthermore, a pointer (indicating member) 74 is fixed to the end of the tip portion 72-1 and extends into the slot 70. According to the rotational movement of the supporting plate 22 about its axis (center of the pin 24 shown in FIG. 9 or 10), the pointer 74 moves along the graduation or scale 71 in the slot 70 as shown in FIGS. 9 and 10. Therefore, the position of the pointer 74 corresponds to an angle of rotation of the supporting plate 22 to the engaging plate 14. Thus, by the reading value of the scale 71 pointed by the pointer 74, it becomes possible to directly read the angle of rotation, which is equivalent to a deviation from a parallel state of opposing surfaces of the femoral bone and the tibial bone, which corresponds to the value of the ligament balance.

Hereinafter, the measurement of a joint gap and a ligament balance by the measuring apparatus according to the present invention will be explained. FIG. 9 schematically illustrates a anterior view of a structure of a tibiofemoral joint, where a patella P drawn in phantom lines is positioned on this side of a femoral bone F and a tibial bone T, the upper portion of the patella P is connected to the femoral bone F by a quadriceps femoris tendon Q and the lower portion of the patella P is connected to the tibial bone T by a patellar tendon L. In FIG. 9, EA and EB schematically illustrate a media collateral ligament and lateral collateral ligament (soft tissues), respectively, which are positioned on the inside and the outside of a knee and connect the femoral bone F and the tibial bone T. FIG. 9 illustrates a total knee replacement operation of a left-hand knee joint of a patient, where a skin incision at the beginning of the operation is vertically carried out at approximately the inside of the patella as shown in a broken line 76. After the skin incision, an articular capsule incision is made according to a usual operational method for a joint replacement operation, and the patella P is outwardly everted together with the quadriceps femoris tendon Q and the patellar tendon L that are connected thereto. The everted conditions of the patella, quadriceps femoris tendon and patellar tendon are schematically illustrated by symbols P', Q' and L', respectively in FIG. 9.

As shown in FIG. 7, the femoral bone F is osteotomized by an end surface FA, a posterior surface FB, an anterior surface FC and a slant surface FD that runs from the end surface FA to the anterior surface FC, at its distal end. On the other hand, the tibial bone T is osteotomized flatly by an end surface TA at its proximal end. And then, a trial femoral component having all the same sizes as that of the femoral component to be fitted to the patient is prepared to fit to the femoral bone F of the patient such that an opposed and contacted arrangement is obtained between the surfaces 52A and FA, 52B and FB, 52C and FC, and 52D and FD. As described before with reference to FIG. 9, the patella P is outwardly everted from a skin incision line 76 as shown by P', and the gap between opposing faces of the femoral bone F and the tibial bone T is in an outwardly opened state, where the measuring apparatus of the present invention is installed. As shown in FIGS. 7 and 9, the engaging plate 14 extending from the base 10 via the arm 12 is introduced into the gap between opposing osteotomized surfaces of the femoral bone F and the tibial bone T, and is fixed to the upper surface TA of the tibial bone T by driving the fixing nails 16 downwardly built in the bottom surface of the engaging plate 14. On the other hand, the supporting plate 22 at the end of the arm 20 extending from the moving body 18 is also introduced into the gap between opposing osteotomized surfaces of the femoral bone F and the tibial bone T in the same way as in the above. Thereupon, the raised portion 48 on the supporting plate 22 is fitted with the auxiliary guiding piece 50 matched to the particular femoral component 52 for trial use for a patient. Then, the supporting plate 22 is introduced so that the auxiliary guiding piece 50 is positioned in the guiding channel 54 of the trial femoral component 52. After the insertion of the engaging plate 14 and the supporting plate 22 into the gap between opposing osteotomized surfaces of the femoral bone F and the tibial bone T as the above explained, the patella eversion as shown by the phantom line P'in FIG. 9 is cancelled, i.e., the patella is returned to its original position facing ahead as shown by the phantom line P in FIG. 9. In the present invention, the engaging plate 14 and the supporting plate 22 are under an offset relationship with respect to the base 10 and the moving body 18, respectively (refer to FIG. 6 for the offset relationship). That is, as shown in FIG. 9, the base 10 and the moving body 18 are positioned inside of the knee under the condition that the engaging plate 14 and the supporting plate 22 are fitted or inserted to the tibial bone and the femoral bone, respectively. What makes the patella eversion to be unnecessary during the measurement of the joint gap and the ligament balance according to the present invention is this offset arrangement. Namely, the members 10 and 18 do not prevent the patella to be returned to a position directed anteriorly as shown by the phantom line Q. Thus, it becomes to be possible to carry out the measurement under the original physiological state of the knee without any eversion of the patella P.

As stated above, the measurement of a gap and a ligament balance is carried out under the patella P restored into its original position facing ahead. To be more precise, in FIG. 1, the tip, which has a hexagonal section, of the torque wrench 46 is inserted into the tool engaging cutout 44 on the end surface of the ratchet wheel 36 to apply a torque in the direction as shown by the arrow f1 in FIGS. 1 and 2 to the ratchet wheel 36. A step like rotating movement of the ratchet wheel 36 is obtained each time when the tooth 36-1 of the ratchet wheel 36 climbs over the pawl portion 38-1 at the end of the ratchet lever 38. In other words, a step like movement or raise of the supporting shaft 26 is obtained in the direction as shown by the arrow h direction in FIG. 9 via the toothed wheel 32 and the rack 34. In FIG. 7, the upward movement of the supporting shaft 26 increases the gap between the supporting plate 22 at the end of the arm 20 extending from the top of the supporting shaft 26 and the engaging plate 14 at the end of the arm 12 extending from the base 10, which causes the femoral bone F on the side of the supporting plate 22 and the tibial bone T on the side of the engaging plate 14 to be distant, so that the media collateral ligament EA and the lateral collateral ligament EB connecting the femoral bone F and the tibial bone T, the quadriceps femoris tendon Q and the patellar tendon L are subjected to a stretching. When a torque value in correspondence with the tension reaches to a predetermined value, the torque wrench 46 shown in FIG. 1 idles and the ratchet wheel 36 cannot rotate more than that, meanwhile, the ratchet wheel 36 is prevented from being rotated in the direction as shown by the arrow f2 due to an engagement of the tooth 36-1 with the pawl portion 38-1 of the ratchet lever 38, so that the engaging plate 14 and the supporting plate 22 are maintained under the condition where a load in correspondence with a predetermined torque is applied. In this state, a scale reading of the graduation or scale 66 pointed by the same plane as that of the base 10 in FIG. 1 is a value of the gap between the end surface FA of the femoral bone F and the end surface TA of the tibial bone T in a knee extended state shown in FIG. 7. Also, an angle of inclination between the end surface FA of the femoral bone F and the end surface TA of the tibial bone T, which corresponds to a ligament balance, can be read by the graduation 71. FIG. 9 illustrates the ligament balanced condition under the knee extended condition, where the supporting plate 22 is parallel to the engaging plate 14 due to the fact that the osteotomized surfaces FA and TA are parallel to each other. In this case, the pointer 74 at the tip of the arm 72 extending from the supporting plate 22 reads a center of the graduation 71. On the other hand, under a condition where a ligament balance is not obtained, some degree of an inclination of the supporting plate 22 with respect to the engaging plate 14 is obtained as shown in FIG. 10, and the degree of imbalance can be immediately read on the graduation 71 pointed by the pointer 74. Note that, in order to correct the gap and the ligament balance, the resection or relaxation operation of both of the media collateral ligament EA and the lateral collateral ligament EB (soft tissues) is carried out according to a usual operational method for a joint replacement operation.

FIG. 8 shows a measuring state in accordance with the measuring apparatus of the present invention under the conditions that the femoral bone F is flexed with respect to the tibial bone T, so that the flat osteotomized surface FB is parallel to the osteotomized surface TA of the tibial bone T. In this state, the femoral component 52 above the supporting plate 22 has accepted by its guiding channel 54 by way of the auxiliary guiding piece 50 fitted to the raised portion 48 of the supporting plate 22. Owing to this, the guiding function by virtue of the auxiliary guiding piece 50 above the supporting plate 22 allows the femoral bone F to flex with respect to the tibial bone T. Namely, also in the flexed state shown in FIG. 8, it is possible by using the measuring apparatus to measure the gap between the flat osteotomized surface FB in the back of the femoral bone and the osteotomized surface TA at the end of the tibial bone and an angle of inclination (ligament balance) between these faces FB and TA.

In the present invention, an angle of the supporting plate 22 with respect to the engaging plate 14 is measured under the conditions that the femoral component 52 is fitted to the femoral bone and supported on the supporting plate 22 via the auxiliary guiding piece 50 as a guiding member, therefore, it is possible to carry out measurement under any desired knee angle. That is, the auxiliary guiding piece 50 on the raised portion 48 of the supporting plate 22 is protruded in the guiding channel 54 of the femoral component 52, which allows the femoral component 52 to flex and extend within a predetermined angle range according to the guidance by the auxiliary guiding piece 50. Therefore, it is possible to measure the gap and the ligament balance between the engaging plate 14 and the supporting plate 22 under any desired value of the knee flexion angle. Furthermore, it becomes possible to measure the gap under the extended state, which the measurement does not depend on the state of osteotomized surfaces and was impossible in the prior art described in U.S. Pat. No. 5,911,723 of Ashby et al. That is, in the technique described in Ashby et al., the measurement was carried out by directly engaging the engaging surfaces of the measuring apparatus with osteotomized surfaces of the tibial bone and the femoral bone. However, the osteotomized surface TA of the tibial bone does not orthogonally cross the bone axis due to a structure of the femoral component and is somewhat inclined, while the osteotomized surface FA of the femoral bone orthogonally crosses the bone axis. Owing to this, it was possible to measure only the extended state of a knee joint, which the measurement depends on conditions of opposing osteotomized surfaces of the femoral bone and the tibial bone. On the other hand, in the present invention, the measurement is carried out under the conditions that the femoral component 52 is fit to the femoral bone and supported on the supporting plate 22. Therefore, it becomes now possible to carry out the measurement of the extended state of a knee joint without depending on the conditions of opposing osteotomized surfaces of the femoral bone and the tibial bone.

Also, in the technique described in Ashby et al., since the engaging surface is fitted to the flat osteotomized surface on the side of the femoral bone, the measurement can be carried out for only two positions, that are an extended condition where the flat osteotomized surface of the tibial bone is parallel with respect to the flat osteotomized surface at the end of the femoral bone and a flexed condition where the flat osteotomized surface on the posterior side of the femoral bone is parallel with respect to the flat osteotomized surface of the tibial bone. However, in the present invention, owing to the femoral component at the end of the femoral bone to be fitted to the supporting plate 22 of the measuring apparatus, it is possible to carry out the measurement at any knee flexion angle.

Although the present invention has been described with reference to an embodiment, it will be clear that many modifications and changes may be made by those skilled in this art without departing scopes and spirits of the present invention.

The invention claimed is:

1. An apparatus for measuring a joint gap and ligament balance between an osteotomized surface at a distal end of a femur and an osteotomized surface at a proximal end of a tibia, said apparatus comprising:
    a base;
    a first engaging member for an engagement with said osteotomized surface at the proximal end of the tibia;
    a first arm obliquely connecting said base and said first engaging member to have a structure in which said base is configured to be positioned outside an area right in front of the tibia;
    a moving body;
    a second engaging member for an engagement with said osteotomized surface at said distal end of the femur, said second engaging member being rotatable about an axis substantially parallel with respect to said osteotomized surface at the distal end of the femur;
    a second arm obliquely connecting said moving body and said second engaging member to have a structure in which said moving body is configured to be positioned outside an area right in front of the femur;
    said base and said moving body being connected with each other so that the first and second engaging members are selectively moved between a direction where the first and second engaging members are moved toward each other and a direction where the first and second engaging members are moved away from each other;
    a driving member configured to drive said moving body with respect to the base so that the first and second engaging members are moved in the direction away from each other;
    a stopper provided on the moving body and configured to engage with the driving member to restrain movement of the driving member in the direction where the first and second engaging members are moved toward each other;
    a first indicator configured to indicate a value corresponding spacing between the first and second engaging members; and
    a second indicator configured to indicate a value corresponding an angle between the first and second engaging members.

2. An apparatus according to claim 1, wherein said stopper is a ratchet member on the moving body, and wherein said driving member includes a ratchet wheel with which the ratchet member is engaged for preventing the ratchet wheel from being rotated for locking the movement of the driving member in the direction where the first and second engaging members are moved toward each other.

3. An apparatus according to claim 1, wherein said moving body includes a shaft which is inserted to a bore in the base, and wherein said first indicator comprises a scale on the shaft.

4. An apparatus according to claim 1, wherein said second indicator includes a scale plate fixed on an outer side of the moving body and an indicating member extending from the second engaging member toward the scale plate, the indicating member having an end which is located along the scale plate.

5. An apparatus according to claim 1, wherein said moving body includes a shaft disposed a bore in the base.

6. An apparatus for measuring a joint gap and ligament balance between an osteotomized surface at a distal end of a femur and an osteotomized surface at a proximal end of a tibia, said apparatus comprising:
    a femoral component for an insertion to the osteotomized surface at the distal end of the femur;
    a base;
    a first engaging member for an engagement with said osteotomized surface at the proximal end of the tibia;
    a first arm obliquely connecting said base and said first engaging member to have a structure in which said base is configured to be positioned outside an area right in front of the tibia;
    a moving body;
    a second engaging member for an engagement with said osteotomized surface at said distal end of the femur, said second engaging member being for mounting thereon said femoral component, said second engaging member being rotatable about an axis substantially parallel with respect to said osteotomized surface at the distal end of the femur;

a second arm obliquely connecting said moving body and said second engaging member to have a structure in which said moving body is configured to be positioned outside an area right in front of the femur;

said base and said moving body being connected with each other so that the first and second engaging members are selectively moved between a direction where the first and second engaging members are moved toward each other and a direction where the first and second engaging members are moved away from each other;

a driving member configured to move said moving body with respect to the base so that the first and second engaging members are moved in the direction away from each other;

a stopper provided on the moving body and configured to engage with the driving member to restrain movement of the driving member in the direction where the first and second engaging members are moved toward each other;

a first indicator configured to indicate a value corresponding spacing between the first and second engaging members; and a second indicator configured to indicate a value corresponding an angle between the first and second engaging members.

7. An apparatus according to clam 6, wherein said second engaging member has, at a surface remote from the first engaging member, a fitting part, and wherein the apparatus further comprises an auxiliary guiding member for a fitting engagement with said fitting part on the second engaging member and engaged with the femoral component.

8. An apparatus according to claim 7, wherein said fitting engagement between the fitting part of the second engaging member and the auxiliary guiding member is done under a snap engaging fashion.

9. An apparatus according to claim 6, wherein said stopper is a ratchet member on the moving body, and wherein said driving member includes a ratchet wheel with which the ratchet member is engaged for preventing the ratchet wheel from being rotated for locking a movement of the driving member in the direction where the first and second engaging members are moved toward each other.

10. An apparatus according to claim 6, wherein said moving body includes a shaft which is inserted to a bore in the base, and wherein said first indicator comprises a scale on the shaft.

11. An apparatus according to claim 6, wherein said second indicator includes a scale plate fixed on an outer side of the moving body and an indicating member extending from the second engaging member toward an indicator plat, the indicating member having an end which is located along the scale plate.

* * * * *